United States Patent
Oda et al.

(10) Patent No.: US 12,281,059 B2
(45) Date of Patent: Apr. 22, 2025

(54) METHOD FOR PRODUCING HALOGENATED HYDROCARBON MAGNESIUM COMPOUND AND METHODS FOR PRODUCING TERTIARY ALCOHOL COMPOUND AND ORGANOSILICON COMPOUND

(71) Applicant: TOKUYAMA CORPORATION, Yamaguchi (JP)

(72) Inventors: Hiroyuki Oda, Yamaguchi (JP); Ryosuke Nishimoto, Yamaguchi (JP); Daisuke Abiko, Yamaguchi (JP); Takenori Isomura, Yamaguchi (JP)

(73) Assignee: TOKUYAMA CORPORATION, Yamaguchi (JP)

( * ) Notice: Subject to any disclaimer, the term of this patent is extended or adjusted under 35 U.S.C. 154(b) by 218 days.

(21) Appl. No.: 17/795,207

(22) PCT Filed: Jan. 21, 2021

(86) PCT No.: PCT/JP2021/002091
§ 371 (c)(1),
(2) Date: Jul. 25, 2022

(87) PCT Pub. No.: WO2021/153422
PCT Pub. Date: Aug. 5, 2021

(65) Prior Publication Data
US 2023/0050880 A1 Feb. 16, 2023

(30) Foreign Application Priority Data
Jan. 27, 2020 (JP) .................................. 2020-011213

(51) Int. Cl.
C07C 29/40 (2006.01)
C07F 3/02 (2006.01)
C07F 7/12 (2006.01)
C07F 7/18 (2006.01)

(52) U.S. Cl.
CPC ................ *C07C 29/40* (2013.01); *C07F 3/02* (2013.01); *C07F 7/12* (2013.01); *C07F 7/1804* (2013.01)

(58) Field of Classification Search
CPC ......... C07C 29/40; C07C 31/125; C07F 3/02; C07F 7/12; C07F 7/1804
See application file for complete search history.

(56) References Cited

U.S. PATENT DOCUMENTS

| 4,105,703 A | 8/1978 | Motta et al. |
| 4,485,035 A | 11/1984 | Shiga et al. |
| 5,872,274 A | 2/1999 | Cannady et al. |
| 6,057,480 A | 5/2000 | Ueno et al. |
| 2016/0137669 A1* | 5/2016 | Thathagar ............ C07D 257/02 260/665 G |

FOREIGN PATENT DOCUMENTS

| CN | 102093396 A | 6/2011 |
| EP | 2248819 A1 | 11/2010 |
| JP | S52057148 A | 5/1977 |
| JP | H09227574 A | 9/1997 |
| JP | 2000044581 A | 2/2000 |
| JP | 2000229982 A | 8/2000 |
| JP | 3779452 B2 | 5/2006 |
| JP | 2007290973 A | 11/2007 |
| JP | 2009114166 A | 5/2009 |
| JP | 2016525504 A | 8/2016 |

OTHER PUBLICATIONS

International Search Report issued in corresponding International Application No. PCT/JP2021/002091; mailed Feb. 25, 2021 (3 pages).
Written Opinion of the International Searching Authority issued in corresponding International Application No. PCT/JP2021/002091; dated Feb. 25, 2021 (4 pages).
Bartmann Ekkehard et al: "Active Magnesium from Catalytically Prepared Magnesium Hydride or from Magnesium Anthracene and its Uses in Synthesis", Chemische Berichte, vol. 123, No. 7, Jul. 1, 1990 (Jul. 1, 1990), pp. 1517-1528 (13 pages).

* cited by examiner

Primary Examiner — Pancham Bakshi
(74) Attorney, Agent, or Firm — Osha Bergman Watanabe & Burton LLP

(57) ABSTRACT

Provided is a method for producing a halogenated hydrocarbon magnesium compound, the method including bringing a halogenated hydrocarbon compound into contact with magnesium having a specific surface area of $1\times10^{-5}$ to $2\times10^{-4}$ m$^2$/g. Also provided are methods for producing a tertiary alcohol compound and an organosilicon compound, wherein said production method is utilized.

11 Claims, No Drawings

METHOD FOR PRODUCING HALOGENATED HYDROCARBON MAGNESIUM COMPOUND AND METHODS FOR PRODUCING TERTIARY ALCOHOL COMPOUND AND ORGANOSILICON COMPOUND

TECHNICAL FIELD

The present invention relates to a method for producing a halogenated hydrocarbon magnesium compound and a method for producing a tertiary alcohol compound and an organosilicon compound.

BACKGROUND ART

Halogenated hydrocarbon magnesium compounds are organometallic compounds used in Grignard reaction. The Grignard reaction is widely used in the synthesis of various organic compounds as a carbon-carbon bond reaction (see Patent Documents 1 and 2). Among halogenated hydrocarbon magnesium compounds, relatively stable compounds, such as methylmagnesium bromide, are commercially available as tetrahydrofuran solutions. Further, the halogenated hydrocarbon magnesium compound can be industrially produced by reacting a halogenated hydrocarbon compound with magnesium in a solvent such as diethyl ether.

As a method for producing the halogenated hydrocarbon magnesium compound, as described in Patent Documents 1 and 2, a production method by a batch method is known, in which magnesium is dispersed in an organic solvent, then iodine or the like is added to activate magnesium (that is, an oxide film on the surface of magnesium is removed), then a solution containing a halogenated hydrocarbon compound is added dropwise, and the halogenated hydrocarbon magnesium compound is produced. Generally, the halogenated hydrocarbon magnesium compound has high reaction activity, but in many cases, the stability of the compound itself is low. Thus, it is necessary to complete the reaction of the halogenated hydrocarbon compound with magnesium in a short time and to supply the resulting halogenated hydrocarbon magnesium compound to the subsequent reaction. Moreover, when magnesium remains in the reaction system, it can be a cause of side reactions during the subsequent reaction, and therefore, the reaction is generally proceeded by using an excessive amount of the halogenated hydrocarbon compound with respect to magnesium so that magnesium does not remain. In addition, since the reaction is a solid-liquid reaction, in order to improve the reaction rate, the halogenated hydrocarbon magnesium compound is produced using magnesium having a relatively high specific surface area and an average particle diameter of about 2 mm or less.

Patent Document 1: Japanese Unexamined Patent Application, Publication No. 2009-114166
Patent Document 2: Japanese Patent No. 3779452

DISCLOSURE OF THE INVENTION

Problems to be Solved by the Invention

On the other hand, a synthesis reaction for the halogenated hydrocarbon magnesium compound is considerably exothermic, and control of the synthesis reaction is difficult in some cases due to the heat generation. Therefore, in industrial production, it is necessary to perform the production while controlling the reaction rate by carrying out the reaction in the presence of a large amount of solvent and adjusting a dropping rate of a solution containing the halogenated hydrocarbon compound. Therefore, it is difficult to increase the production amount of the halogenated hydrocarbon magnesium per batch. In addition, since scale-up decreases a heat transfer area of the reaction vessel, there is still room for improvement in terms of heat removal efficiency.

It is an object of the present invention to provide a method for producing a halogenated hydrocarbon magnesium compound, the method enabling the reaction to be carried out under mild conditions.

Means for Solving the Problems

In order to solve the above problem, the present inventors have intensively studied reaction conditions of the halogenated hydrocarbon compound and magnesium. As a result, it was found that there is a correlation between the particle size of magnesium and reaction efficiency, and further, it was found that the reaction can be easily controlled by reducing the specific surface area of magnesium to a specific range. In addition, when the specific surface area of magnesium is reduced, the reaction yield is lowered because the contact ratio between the halogenated hydrocarbon compound and the magnesium surface is reduced. However, the inventors have found that by preparing a packed tower filled with magnesium, and repeatedly passing a solution containing the halogenated hydrocarbon compound through the packed tower, the reaction yield of the halogenated hydrocarbon compound can be improved. The present invention has been completed based on such findings, and specifically, is as follows.

A first aspect relates to a method for producing a halogenated hydrocarbon magnesium compound, the method including contacting a halogenated hydrocarbon compound with magnesium having a specific surface area of $1 \times 10^{-5}$ to $2 \times 10^{-4}$ m$^2$/g.

A second aspect relates to the method for producing a halogenated hydrocarbon magnesium compound as described in the first aspect, in which the halogenated hydrocarbon compound is at least one selected from a mono-halogenated alkyl compound and a di-halogenated alkyl compound represented by the following formula (1):

[Chem. 1]

$$X\text{—}R\text{—}X \qquad (1)$$

(in which R represents a linear or branched alkyl group having 1 to 8 carbon atoms and X represents a halogen atom).

A third aspect relates to the method for producing a halogenated hydrocarbon magnesium compound as described in the first or second aspect, in which the halogenated hydrocarbon compound is a hydrocarbon bromide compound.

A fourth aspect relates to the method for producing a halogenated hydrocarbon magnesium compound as described in any one of the first to third aspects, in which the halogenated hydrocarbon compound is contacted with the magnesium at a temperature between −78° C. and 100° C.

A fifth aspect relates to the method for producing a halogenated hydrocarbon magnesium compound as described in any one of the first to fourth aspects, in which a solution containing the halogenated hydrocarbon compound is contacted with the magnesium.

A sixth aspect relates to the method for producing a halogenated hydrocarbon magnesium compound as described in the fifth aspect, in which the solution containing the halogenated hydrocarbon compound is passed through a packed tower filled with the magnesium.

A seventh aspect relates to the method for producing a halogenated hydrocarbon magnesium compound as described in the sixth aspect, in which the solution containing the halogenated hydrocarbon compound is repeatedly passed through the packed tower filled with the magnesium.

An eighth aspect relates to the method for producing a halogenated hydrocarbon magnesium compound as described in the sixth or seventh aspect, in which a plurality of packed towers each filled with the magnesium exist and the solution containing the halogenated hydrocarbon compound is passed through the plurality of packed towers.

A ninth aspect relates to the method for producing a halogenated hydrocarbon magnesium compound as described in any one of the sixth to eighth aspects, in which the solution containing the halogenated hydrocarbon compound has a temperature between $-78°$ C. and $100°$ C.

A tenth aspect relates to a method for producing a tertiary alcohol compound, including:
  producing a halogenated hydrocarbon magnesium compound by the method as described in any one of the first to ninth aspects, and
  contacting the halogenated hydrocarbon magnesium compound with a ketone compound.

An eleventh aspect relates to a method for producing a tertiary alcohol compound, including contacting a halogenated hydrocarbon compound, a ketone compound, and magnesium having a specific surface area of $1 \times 10^{-5}$ to $2 \times 10^{-4}$ m$^2$/g.

A twelfth aspect relates to a method for producing an organosilicon compound, including:
  producing a halogenated hydrocarbon magnesium compound by the production method as described in any one of the first to ninth aspects, and
  contacting the halogenated hydrocarbon magnesium compound with a silicon compound selected from a chlorosilane compound and an alkoxysilane compound.

A thirteenth aspect relates to a method for producing an organosilicon compound, including contacting a halogenated alkyl compound, a silicon compound selected from a chlorosilane compound and an alkoxysilane compound, and magnesium having a specific surface area of $1 \times 10^{-5}$ to $2 \times 10^{-4}$ m$^2$/g.

Effects of the Invention

According to the method for producing a halogenated hydrocarbon magnesium compound of the present invention, by using magnesium having a small specific surface area, it is possible to easily control a reaction between the halogenated hydrocarbon compound and the magnesium. Further, since control of the reaction is easy, scale-up to an industrial production scale is easy. Furthermore, by preparing a packed tower filled with magnesium and repeatedly passing a solution containing a halogenated hydrocarbon compound through the packed tower, it is possible to improve reaction yield of the halogenated hydrocarbon compound and to produce a halogenated hydrocarbon magnesium compound in a high yield. Moreover, it is possible to continuously pass the solution containing a halogenated hydrocarbon compound through the packed tower filled with magnesium, whereby continuous production of the halogenated hydrocarbon magnesium compound is possible.

Preferred Mode for Carrying Out the Invention

<Method for producing Halogenated Hydrocarbon Magnesium Compound>

The method for producing a halogenated hydrocarbon magnesium compound according to the present embodiment (hereinafter, simply referred to as a "production method according to the present embodiment") includes contacting a halogenated hydrocarbon compound with magnesium having a specific surface area of $1 \times 10^{-5}$ to $2 \times 10^{-4}$ m$^2$/g. Hereinafter, the production method according to the present embodiment will be described in detail.

[Halogenated Hydrocarbon Compounds]

Examples of the halogenated hydrocarbon compound include known compounds such as a hydrocarbon chloride compound, a hydrocarbon bromide compound, and a hydrocarbon iodide compound. Examples of the halogenated hydrocarbon compound include: mono-halogenated alkyl compounds; mono-halogenated alkenyl compounds; mono-halogenated aromatic hydrocarbon compounds such as chlorobenzene, α-chlorotoluene, bromobenzene, α-bromotoluene, iodobenzene, and α-iodotoluene; di-halogenated alkyl compounds represented by the following formula (1):

[Chem. 2]

$$X-R-X \qquad (1)$$

wherein R represents a linear or branched alkyl group having 1 to 8 carbon atoms, and X represents a halogen atom), and di-halogenated aromatic hydrocarbon compounds, such as o-dichlorobenzene, m-dichlorobenzene, p-dichlorobenzene, o-dibromobenzene, m-dibromobenzene, p-dibromobenzene, o-diiodobenzene, m-diiodobenzene, and p-diiodobenzene.

As an alkyl group in the mono-halogenated alkyl compound, a linear or branched alkyl group having 1 to 8 carbon atoms is preferred. Examples of such a mono-halogenated alkyl compound include: chloromethane, chloroethane, chloropropane, 2-chloropropane, 1-chloro-2-methylpropane, 2-chloro methylpropane, 2-bromo-2-methylpropane, chlorobutane, bromobutane, chloropentane, chlorocyclopentane, chlorohexane, bromomethane, bromoethane, bromopropane, 2-bromopropane, 1-bromo-2-methylpropane, bromobutane, bromopentane, bromocyclopentane, bromohexane, iodomethane, iodoethane, iodopropane, 2-iodopropane, 1-iodo-2-methylpropane, 2-iodo-2-methylpropane, iodopentane, iodocyclopentane, and iodohexane.

As an alkenyl group in the mono-halogenated alkenyl compound, a linear or branched alkenyl group having 2 to 8 carbon atoms is preferred. Examples of such mono-halogenated alkenyl compounds include chloroethylene, 3-chloro-1-propene, bromoethylene, 3-bromo-1-propene, iodoethylene, and 3-iodo-1-propene.

R in the formula (1) represents a linear or branched alkyl group having 1 to 8 carbon atoms. Examples of such alkyl groups include a methyl group, an ethyl group, a propyl group, a butyl group, and an isobutyl group. Examples of the di-halogenated alkyl compound represented by the formula (1) include 1,3-dichloropropane, 1,4-dichlorobutane, 1,5-dichloropentane, 1,3-dibromopropane, 1,4-dibromobutane, 1,5-dibromopentane, 1,3-diiodopropane, 1,4-diiodobutane, and 1,5-diiodopentane.

Among these halogenated hydrocarbon compounds, mono-halogenated alkyl compounds and di-halogenated alkyl compounds represented by the formula (1) are preferred from the viewpoint of being useful as a Grignard reagent, and mono-brominated alkyl compounds and dibrominated alkyl compounds are more preferred.

[Organic Solvents]

When the halogenated hydrocarbon compound is a liquid, the halogenated hydrocarbon magnesium compound can be produced by bringing the halogenated hydrocarbon compound into contact with magnesium as it is, but it is preferable to dissolve the halogenated hydrocarbon compound in an organic solvent and use, from the viewpoint of easy control of reaction temperature. Examples of such organic solvents include ether-based solvents such as diethyl ether, diisopropyl ether, dibutyl ether, tert-butyl methyl ether, 1,2-dimethoxyethane, tetrahydrofuran, 2-methyltetrahydrofuran, and 1,4-dioxane. These ether solvents may be used alone, or may be used as a mixed solution of a plurality of these solvents. Among these ether solvents, tetrahydrofuran is preferred from the viewpoint of ease of industrial availability and appropriateness of the boiling point thereof.

Further, since the halogenated hydrocarbon magnesium compound reacts with water and is deactivated, the organic solvent to be used preferably has a low moisture content, specifically, a moisture content of less than 500 ppm, and more preferably less than 100 ppm.

An amount of the organic solvent to be used may be appropriately determined in consideration of scale of production facility, heat removal efficiency, and the like. When the halogenated hydrocarbon compound is a liquid at an ambient temperature, the organic solvent is preferably used in a range of 1 to 99 parts by volume, more preferably in a range of 2 to 98 parts by volume, and most preferably in a range of 3 to 97 parts by volume, per 1 part by volume of the halogenated hydrocarbon compound from the viewpoint of productivity and suppressing salts such as magnesium halide produced as a by-product in the reaction from precipitating. When the halogenated hydrocarbon compound is a solid at an ambient temperature, the organic solvent is preferably used in a range of 1 to 130 parts by mass, more preferably in a range of 2 to 120 parts by mass, and most preferably in a range of 3 to 110 parts by mass, per 1 part by mass of the halogenated hydrocarbon compound from the viewpoint of productivity and suppressing salts such as magnesium halide produced as a by-product in the reaction from precipitating.

[Magnesium]

In the production method according to the present embodiment, magnesium having a specific surface area of $1 \times 10^{-5}$ to $2 \times 10^{-4}$ m$^2$/g is used. Commonly, the specific surface area of magnesium used in the batch method is about $3 \times 10^{-4}$ to $1 \times 10^{-2}$ m$^2$/g. Magnesium used in the present invention is characterized by having a smaller specific surface area than magnesium used in the batch method. By using such magnesium, it is possible to easily control reaction between the halogenated hydrocarbon compound and magnesium. Note that the specific surface area of magnesium in this specification is measured by the method described below.

(Method for Measuring Specific Surface Area of Magnesium)

A surface area of magnesium particles weighed on a precision balance is calculated by measuring the size thereof by an optical microscope at a magnification of 10×, and dividing this surface area by the particle weight. Similar measurements are performed for 10 magnesium particles, and the average thereof is taken as the specific surface area.

Since a contact area between a solution containing the halogenated hydrocarbon compound and magnesium affects the reaction rate, if the specific surface area of magnesium is too small, the reaction will not efficiently proceed. This results in a slow reaction rate, which is unpreferred. If the specific surface area is too large, the reaction rate becomes too large, and there is a risk that the reaction goes out of control and turns uncontrollable. In particular, many ether-based solvents described above have a low boiling point, and there is a risk of bumping or the like when the reaction runs away. From the viewpoint of productivity of the halogenated hydrocarbon magnesium compound, the specific surface area of magnesium is preferably $5 \times 10^{-5}$ to $1 \times 10^{-4}$ m$^2$/g.

The shape of magnesium is not particularly limited, and a pellet shape, a shot shape, a mesh-like shape, a bar-like shape, etc. can be mentioned. Magnesium sometimes contains metal impurities. From the viewpoint of suppressing side reactions caused by metal impurities, the purity of magnesium is preferably 90% or more, and more preferably 99% or more.

Magnesium usually reacts with oxygen in the atmosphere to form an oxide film on the surface, and the oxide film interferes with the reaction with the halogenated hydrocarbon compound. Therefore, in order that the reaction is allowed to smoothly proceed in the initial stage of the reaction, it is preferable to activate magnesium before contacting the magnesium with the halogenated hydrocarbon compound. Examples of the activation treatment of magnesium include a method in which an activating agent such as methyl iodide, dibromoethylene, or dibromoethane is added at the initial stage of the reaction, so that the activating agent reacts with an oxide film on the surface of magnesium; and a method in which magnesium is washed with a dilute hydrochloric acid solution, a dilute nitric acid solution, or the like before use. The addition amount of activating agent is usually sufficient in the range of 5 to 10 mol %, with respect to magnesium.

[Contact Temperature]

The temperature at which the halogenated hydrocarbon compound and magnesium are contacted with each other may be appropriately set at a temperature sufficient for the reaction to proceed. From the viewpoint of reactivity, the contact temperature is preferably in the range of −78 to 100° C., and more preferably in the range of −78 to 60° C. The higher the contact temperature, the higher the reaction rate, while a side reaction between the produced halogenated hydrocarbon magnesium compounds (such as Ultz coupling) tends to occur. On the other hand, when the temperature is too low, the reaction rate decreases, resulting in a longer reaction time. Therefore, the contact temperature may be appropriately selected in consideration of the stability of the targeted halogenated hydrocarbon magnesium compound.

[Production Method by Batch Method]

The production method according to the present embodiment can be carried out in a reaction vessel equipped with a stirrer. There is no particular limitation on the method of contacting the halogenated hydrocarbon compound with magnesium. Examples include: 1) a method including charging an organic solvent and magnesium into a reaction vessel, adding an activating agent to activate magnesium, then heating the solution to the above-described contact temperature, and adding a halogenated hydrocarbon compound dissolved in an organic solvent while stirring the solution; and 2) a method including charging an organic solvent, a halogenated hydrocarbon compound, and an activating agent into a reaction vessel, dissolving the halogenated hydrocarbon compound in the organic solvent, then heating the solution to the above-described contact temperature, and adding magnesium. Addition of the solution containing a halogenated hydrocarbon compound in method 1) or addition of magnesium in method 2) is preferably carried out while confirming the temperature in the reaction vessel so as not to exceed the predetermined contact temperature. Specifically, in method 1), it is preferable to adjust the dropwise addition rate of the solution containing a halogenated hydrocarbon compound. In the above method 2), it is preferable to add magnesium in a plurality of additions.

When the halogenated hydrocarbon magnesium compound to be produced is relatively unstable, it is preferable to produce the halogenated hydrocarbon magnesium compound in the presence of a ketone compound or a silicon compound (chlorosilane compound, alkoxysilane compound), which will be described later, because the produced halogenated hydrocarbon magnesium compound can react with the ketone compound or the silicon compound. Examples of methods for allowing a ketone compound or a silicon compound to coexist in method 1) include: a method in which a ketone compound or a silicon compound is charged together with magnesium in advance into a reaction vessel and a solution containing a halogenated hydrocarbon compound is added; and a method in which a ketone compound or a silicon compound is added to a solution containing a halogenated hydrocarbon compound, and the obtained solution is added to a reaction vessel. With respect to method 2), a method in which an organic solvent, a halogenated hydrocarbon compound, a ketone compound or a silicon compound are charged into a reaction vessel in advance and mixed, and then magnesium is added can be mentioned.

The used amount of a ketone compound or a silicon compound may be appropriately determined in consideration of reactivity with the halogenated hydrocarbon magnesium compound produced. Usually, the ketone compound or the silicon compound may be appropriately used in a range of 1 to 2.5 mol with respect to 1 mol of the halogenated alkyl compound.

The used amount of magnesium may be appropriately determined in consideration of reactivity with the halogenated hydrocarbon compound, and usually, may be appropriately determined in the range of 1 to 1.5 mol with respect to 1 mol of halogen atoms of the halogenated hydrocarbon compound. When the halogenated hydrocarbon compound is a dihalogenated hydrocarbon compound, theoretically, 2 mol of magnesium is required per 1 mol of the dihalogenated hydrocarbon compound, and the used amount is usually appropriately determined in the range of 2 to 2.5 mol.

The reaction atmosphere is preferably an inert atmosphere of nitrogen or argon.

The reaction time may be appropriately determined while confirming a conversion ratio to the halogenated hydrocarbon magnesium compound as a product. The reaction time is usually from 1 to 24 hours, and preferably from 3 to 12 hours.

When magnesium remains after completion of the reaction, the magnesium can be used for the next reaction after removing the magnesium by filtration or the like. When a ketone compound or a silicon compound is mixed in the solution containing a halogenated hydrocarbon compound, a corresponding tertiary alcohol or an organosilane compound is generated, respectively. Therefore, it is possible to purify by a known means after adding an acid after completion of the reaction to decompose an unreacted halogenated hydrocarbon magnesium compound.

[Production Method by Packed Tower Flow Method]

In the production method according to the present embodiment, a method in which a packed tower filled with magnesium (hereinafter, also referred to as a "magnesium packed tower") is prepared, and a solution containing a halogenated hydrocarbon compound is passed through the packed tower, whereby the halogenated hydrocarbon compound is contacted with magnesium, and a halogenated hydrocarbon magnesium compound is produced, can be employed. Hereinafter, the method including passing a liquid through a magnesium packed tower is referred to as a "packed tower flow method". In the packed tower flow method, a solution containing a halogenated hydrocarbon compound is supplied from one end of the packed tower and discharged from the other end of the packed tower, during which the halogenated hydrocarbon compound is in contact with magnesium in the packed tower. Therefore, according to the packed tower flow method, it is possible to control the reaction temperature by shortening the contact time between the halogenated hydrocarbon compound and magnesium. In addition, in the packed tower flow method, it is possible to continuously supply a solution containing a halogenated hydrocarbon compound to the packed tower. Therefore, the packed tower flow method can improve productivity of the halogenated hydrocarbon magnesium compound. Hereinafter, a method for producing the halogenated hydrocarbon magnesium compound by the packed tower flow method will be described in detail.

(Magnesium)

In the packed tower flow method, the packed tower is filled with magnesium with a specific surface area of $1 \times 10^{-5}$ to $2 \times 10^{-4}$ m$^2$/g. At this time, if the specific surface area of magnesium in the packed tower is too large, the contact area of magnesium with the halogenated hydrocarbon compound supplied to the packed tower is too large. This makes it difficult to control the reaction, which is not preferable. If the specific surface area of magnesium is too small, the reaction efficiency is greatly reduced, which is not preferable. The magnesium filled in the packed tower preferably has a specific surface area of $5 \times 10^{-5}$ to $1 \times 10^{-4}$ m$^2$/g from the viewpoint of balance between the control of reaction and the reaction yield. In addition, for the purpose of enhancing reactivity, it is preferable to use magnesium subjected to an activation treatment in advance.

(Packed Tower)

The packed tower may be any tower that can receive magnesium partially or wholly inside a flow path thereof, the tower being able to allow a solution containing a halogenated hydrocarbon to flow through. The cross-sectional shape of the flow path is preferably circular, and the packed tower preferably has a straight structure including neither branching nor bending inside is preferred. The cross-sectional shape of the flow path is preferably circle with a diameter of 5 to 50 mm from the viewpoint of increasing evenness of flux in the cross-sectional area direction and that of the contact area with magnesium. When the cross-sectional area of the flow path is small, a pressure loss in flowing the solution containing a halogenated hydrocarbon compound tends to be larger, and when the cross-sectional area of the flow path is large, the solution containing a halogenated hydrocarbon compound tends to be uneven due to generation of a vortex flow or the like. From the viewpoint of balance between the control of reaction and the reaction yield, the packed tower more preferably has a diameter of 10 to 30 mm. The length of the packed tower is not particularly limited, and may be appropriately selected so that the temperature in the packed tower when the solution containing a halogenated hydrocarbon compound is passed through and brought into contact with magnesium falls within the range of the contact temperature described above. When the packed tower is excessively long, pressure loss in flowing the solution containing a halogenated hydrocarbon compound tends to be large, and therefore, it may be appropriately selected in the range of 5 to 100 cm. The packed tower may be provided with a cooling function such as a jacket for circulating refrigerant, a Peltier device method, or the like. Although there is no particular limitation on the material of the packed tower, a fluororesin such as polytetrafluoroethylene resin or stainless steel is preferred from the viewpoint of chemical resistance and safety.

Although a filling ratio of magnesium filled in the packed tower is not particularly limited, if the filling ratio is too low, the contact ratio of the halogenated hydrocarbon compound and magnesium tends to decrease, and if the filling ratio is too high, the pressure loss tends to increase when the solution containing a halogenated hydrocarbon compound is passed. Therefore, the filling ratio may be appropriately set in a range in which an occupied volume ratio of magnesium to the internal volume of the packed tower becomes 10 to 80%.

(Solution containing Halogenated Hydrocarbon Compound)

The solution containing a halogenated hydrocarbon compound can be prepared by dissolving a halogenated hydrocarbon compound in an organic solvent described above to obtain a solution. Further, the solution containing a halogenated hydrocarbon compound and a ketone compound or a silicon compound (chlorosilane compound, alkoxysilane compound), which will be described later, may be supplied to the magnesium packed tower. When the halogenated hydrocarbon magnesium compound is relatively unstable, it is preferable to allow a ketone compound or a silicon compound to exist in advance, because the produced halogenated hydrocarbon magnesium compound can react with the ketone compound or the silicon compound.

The used amount of a ketone compound or a silicon compound may be appropriately determined in consideration of reactivity with the halogenated hydrocarbon magnesium compound produced. Usually, the ketone compound or the silicon compound may be appropriately used in a range of 1 to 2.5 mol with respect to 1 mol of the halogenated hydrocarbon compound.

The concentration of a halogenated hydrocarbon compound in the solution containing a halogenated hydrocarbon compound may be appropriately determined in consideration of reactivity of the halogenated hydrocarbon compound used, solubility of the produced halogenated hydrocarbon magnesium compound in an organic solvent, and the like. When the halogenated hydrocarbon compound is liquid at an ambient temperature, it is preferable to use an organic solvent in a range of 1 to 99 parts by volume per 1 part by volume of the halogenated hydrocarbon compound, more preferably in a range of 2 to 98 parts by volume, and most preferably in a range of 3 to 97 parts by volume. When the halogenated hydrocarbon compound is solid at an ambient temperature, it is preferable to use an organic solvent in a range of 1 to 130 parts by mass, more preferably in a range of 2 to 120 parts by mass, and most preferably in a range of 3 to 110 parts by mass, per 1 part by mass of the halogenated hydrocarbon compound.

(Production of Halogenated Hydrocarbon Magnesium Compound by Packed Tower Flow Method)

The contact temperature of the halogenated hydrocarbon compound and magnesium may be appropriately determined in the range of contact temperature described above in consideration of reactivity and the like. When the desired contact temperature is room temperature or higher, the solution containing a halogenated hydrocarbon compound may be heated and supplied to the magnesium packed tower.

A supply rate of the solution containing a halogenated hydrocarbon compound may be appropriately determined in consideration of reaction yields, degrees of temperature increase in the magnesium packed tower, and the like. For example, when a magnesium packed tower having a diameter of 5 to 50 mm, a height of 0.1 to 1 m, and a filling ratio of 10 to 80% is used, a supply rate of a solution containing a halogenated hydrocarbon compound is preferably 10 to 2,000 mL/min, and more preferably 50 to 1,000 mL/min.

As a residence time of a solution containing a halogenated hydrocarbon compound in the magnesium packed tower is longer, the reaction yield tends to be higher, but an increase in the temperature due to reaction heat also tends to be considerable. Therefore, the residence time may be appropriately determined in consideration of the reaction yield of the solution having passed through the magnesium packed tower, the temperature increase in the magnesium packed tower, and the like. For example, when a magnesium packed tower having a diameter of 5 to 50 mm, a height of 0.1 to 1 m, and a filling rate of 10 to 80% is used, the residence time is preferably in the range of 0.1 to 30 seconds, and more preferably in the range of 0.2 to 20 seconds.

By the packed tower flow method, the halogenated hydrocarbon magnesium compound can be produced. In addition, when a ketone compound or a silicon compound is mixed in the solution containing a halogenated hydrocarbon compound, the generated halogenated hydrocarbon magnesium compound reacts with the ketone compound or the silicon compound to produce a corresponding tertiary alcohol or an organosilane compound.

When yields of the halogenated hydrocarbon magnesium compound, the tertiary alcohol, or the organosilicon compound in the reaction liquid having passed through the magnesium packed tower are low, the reaction yields can be increased by repeatedly supplying the reaction liquid to the magnesium packed tower. Alternatively, the reaction yields can be increased by preparing a plurality of magnesium packed towers in series, and supplying a reaction solution after having passed through a tower to another magnesium packed tower. In a case in which a reaction liquid is repeatedly supplied to the magnesium packed tower or a reaction liquid is supplied to another magnesium packed tower, if the temperature of the reaction liquid is high, the reaction liquid may be cooled and then supplied to the magnesium packed tower. The number of magnesium packed towers to be connected in series may be determined depending upon the yield of a desired halogenated hydrocarbon magnesium compound. When the number of the packed towers is increased, a large pressure is required to supply the reaction liquid at a predetermined supply rate, and there is a risk that the production facility becomes large in size. For this reason, from the viewpoint of economical efficiency, the number of packed towers is preferably from 2 to 20, and more preferably from 2 to 15. An end of the reaction, that is, an end of supply of the reaction liquid to the magnesium packed tower, may be determined by confirming the reaction yield of the product in the reaction liquid discharged from the magnesium packed tower.

After completion of the reaction, the reaction solution is collected and can be used for the subsequent reaction. In addition, in the case in which a ketone compound or a silicon compound has been mixed in the solution containing a halogenated hydrocarbon compound, a corresponding tertiary alcohol or an organosilane compound is generated. Therefore, after the completion of reaction, acid is added to decompose an unreacted halogenated hydrocarbon magnesium compound, and then purification by a known means is possible.

<Method for Producing Tertiary Alcohol Compound or Organosilane Compound>

By reacting the halogenated hydrocarbon magnesium compound obtained by the above-described production method with a ketone compound or a silicon compound, a corresponding tertiary alcohol or organosilane compound can be produced. As the ketone compound or silicon compound, compounds used in the Grignard reaction can be used without any particular limitation.

Examples of the ketone compounds include: acetone, methyl ethyl ketone, diethyl ketone, methyl propyl ketone, ethyl propyl ketone, dipropyl ketone, methyl butyl ketone, ethyl butyl ketone, propyl butyl ketone, dibutyl ketone, methyl isopropyl ketone, ethyl isopropyl ketone, diisopropyl ketone, methyl isobutyl ketone, ethyl isobutyl ketone, diisobutyl ketone, propyl isobutyl ketone, methyl vinyl ketone, cyclohexanone, 2-methylcyclopentanone, acetophenone, and benzophenone. Examples of the silicon compounds include: chlorosilane compounds, such as dimethyldichlorosilane, methyltrichlorosilane, trimethylchlorosilane, methyldichlorosilane, vinyltrichlorosilane, phenyltrichlorosilane, and trichlorosilane; and alkoxysilane compounds, such as methyltrimethoxysilane, dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyltriethoxysilane, and octyltriethoxysilane. These ketone compounds or silicon compounds may be used alone, or two or more types thereof may be used in combination, but from the viewpoint of easy purification after the reaction, it is preferable to use one type alone.

The used amount of the ketone compound or the silicon compound may be an amount required to complete the reaction, and usually, the ketone compound or the silicon compound may be appropriately used in a range of 1 to 2.5 mol with respect to 1 mol of the halogenated hydrocarbon magnesium compound.

There is no particular limitation on the reaction method. The ketone compound or the silicon compound may be added to the reaction solution after production of the halogenated hydrocarbon magnesium compound, or an organic solvent and the ketone compound or the silicon compound may be charged into the reaction vessel and mixed, and then a reaction solution after production of the halogenated hydrocarbon magnesium compound may be added.

The reaction temperature may be appropriately determined in consideration of reactivity of the halogenated hydrocarbon magnesium compound with the ketone compound or the silicon compound, and commonly, may be appropriately determined in the range of −78 to 60° C. The reaction time may be also appropriately determined in consideration of the reaction yield, and commonly, may be appropriately determined in a range of 1 to 24 hours. After the completion of reaction, acid is added to decompose an unreacted halogenated hydrocarbon magnesium compound, and then purification by a known means is possible.

EXAMPLES

Hereinafter, representative examples of the present invention will be shown and specifically described, but the present invention is not limited thereto in any way. In the analysis of components in the Examples and Comparative Examples, a gas chromatograph device (manufactured by Agilent Co., Ltd., 6890N) was used. As an analysis column, column DB-1 manufactured by J&W was used. Further, specific surface areas of magnesium in the Examples and Comparative Examples were determined by measuring weights and surface areas per particle using a precision balance and optical microscope observation with a magnification of 10 times as described above, calculating the specific surface area of each particle, and then calculating an average value of 10 particles.

Example 1

To a well-dried 2 L three necked flask, 800 mL of tetrahydrofuran (water content: 10 ppm) and 4.0 g of granular magnesium having an average specific surface area of $5.8 \times 10^{-5}$ m$^2$/g were charged, and a mixed solution of 200 mL of tetrahydrofuran (water content: 10 ppm) and 14.8 g of 1-bromopropane was added dropwise using a dropping tube while stirring with a magnetic stirrer. Since the solution generated heat with the dropping, the dropping rate was adjusted so that the temperature of the reaction solution was maintained at 55° C. while cooling the flask in a water bath, and the dropping was completed over 2 hours. After completion of the dropwise addition, the conversion ratio to propylmagnesium bromide was determined by analyzing propylmagnesium bromide using gas chromatography, and the conversion ratio was found to be 83%.

Example 2

To a well-dried 500 mL glass three necked flask, 200 mL of tetrahydrofuran and 2.4 g of methyl ethyl ketone were charged, and a mixed solution of 5 g of propylmagnesium bromide synthesized in Example 1 and 100 mL of tetrahydrofuran was added dropwise over 1 hour under an argon atmosphere using a dropping tube. $^1$H-NMR of the reaction product confirmed that 2-ethyl-2-pentanol was produced. The synthesis yield was confirmed using gas chromatography, and found to be 72%.

Example 3

To a well-dried 500 mL glass three necked flask, 200 mL of tetrahydrofuran and 4.4 g of dichlorodimethylsilane were charged, and a mixed solution of 5 g of propylmagnesium bromide synthesized in Example 1 and 100 mL of tetrahydrofuran was added dropwise over 1 hour under an argon atmosphere using a dropping tube. $^1$H-NMR of the reaction product confirmed that chlorodimethylpropylsilane was produced. The yield was confirmed by gas chromatography, and the synthesis yield was found to be 76%.

<Preparation of Magnesium Packed Tower>

The magnesium packed towers used in the following Examples had a straight tube structure having an internal flow path length of 200 mm and a circular cross section of 20 mm in diameter, and was made of a polytetrafluoroethylene resin. When passing a liquid through the magnesium packed tower, the packed tower was held and fixed vertically, and liquid passing was carried out in a manner that the liquid was introduced into the tower from the lower part of the flow path and came out of the upper part. Additionally, the packed tower was provided with type K thermocouple inserted from the side surface in the lower part of the packed tower, which is the inlet of liquid, and in the upper part, which is the outlet, so that temperatures at the inlet and outlet of the packed tower could be measured. Supply of a liquid to the magnesium packed tower was carried out using a plunger pump having a liquid contact portion made of polytetrafluoroethylene, regardless of the number of connected packed towers. ¼ inch PFA tubes were used for connecting from the pump to the packed tower and connecting between packed towers, when multiple packed towers were used.

Example 4

To a well-dried 10 L glass bottle, 7.5 L of tetrahydrofuran (water content: 10 ppm) and 150 g of 1-bromopropane were charged and mixed by shaking. The glass bottle was placed in a water bath at 30° C. After the magnesium packed tower was filled with 6.0 g of granular magnesium having an average specific surface area of $5.8 \times 10^{-5}$ m$^2$/g, the mixed solution in the 10 L glass bottle was supplied at a constant flow rate of 400 mL/min, and the magnesium and the solution were brought into contact with each other. During the solution supply, the solution temperature at the outlet of the packed tower was measured with the thermocouple, to be 42° C. to 45° C. The conversion ratio to propylmagnesium bromide was confirmed by analysis of the solution by gas chromatography, and found to be 7%. The solution was passed through the magnesium packed tower under the same conditions. The conversion ratio to propylmagnesium bromide in the solution having passed the packed tower was analyzed by gas chromatography and was confirmed to be 13%.

Example 5

Four magnesium packed towers described above were connected in series using PFA tubes, and the tubes connecting the packed towers were each immersed in a water bath at 30° C., so that the liquid temperature at the inlet of the second or later tubes was 30° C. The mixed solution of tetrahydrofuran and 1-bromopropane described in Example 4 was supplied at 400 mL/min, and the mixed solution was brought into contact with magnesium in each packed tower. During the solution supply, the sample immediately after passing through each packed tower was taken from the sampling valve provided between the packed towers, and the conversion ratio to propylmagnesium bromide was confirmed by analysis by gas chromatography. The conversion ratio was 8% after passing the first tower, 15% after passing the second tower, 24% after passing the third tower, and 33% after passing the fourth tower.

Example 6

The total amount of the solution obtained in Example 5 was further supplied into the four magnesium packed towers connected in series under the same conditions as Example 5 two times. The conversion ratios were 62% after the first supply and 87% after the second supply.

Example 7

To a well-dried 10 L glass bottle, 7.5 L of tetrahydrofuran (water content: 10 ppm), 150 g of 1-bromopropane, and 157 g of dichlorodimethylsilane were charged and mixed by shaking. The resulting mixed solution was supplied to the four magnesium packed towers connected in series under the same conditions as Example 5 three times. Each time the solution was passed through the four magnesium packed towers, a sample was collected and the conversion ratio of the raw material to chlorodimethylpropylsilane was measured by gas chromatography. The conversion ratio was 28% after the first supply, 54% after the second supply, and 84% after the third supply. The temperatures and the results of conversion ratios of the solution discharged from the magnesium packed towers in Example 7 are shown in Table 1.

Example 8

To a well-dried 10 L glass bottle, 7.5 L of tetrahydrofuran (water content: 10 ppm), 246 g of 1,3-dibromopropane, and 315 g of dichlorodimethylsilane were weighed and mixed by shaking. The resulting mixed solution was supplied into four magnesium packed towers connected in series under the same conditions as Example 5 three times. Each time the solution was passed through the four magnesium packed towers, a sample was collected and subjected to analysis. $^1$H-NMR and $^{29}$Si-NMR analyses of the solutions after the reaction confirmed that the product was 1,3-di-(dimethylchlorosilyl)propane. The conversion ratio at each stage was determined by the internal standard method (internal standard substance was toluene) according to $^1$H-NMR. As a result, the conversion ratio was 26% after the first supply, 49% after the second supply, and 71% after the third supply.

Example 9

To a well-dried 10 L glass bottle, 7.5 L of tetrahydrofuran (water content: 10 ppm) and 150 g of 1-bromopropane were weighed and mixed by shaking. The glass bottle was placed in a water bath at 30° C. After the magnesium packed tower was filled with 6.0 g of granular magnesium having an average specific surface area of $9.0 \times 10^{-5}$ m$^2$/g, the mixed solution in the 10 L glass bottle was supplied at a constant flow rate of 400 mL/min, and the magnesium and the solution were brought into contact with each other. During the solution supply, the temperature of the solution at the outlet of the packed tower was measured with a thermocouple, to be 48° C. to 52° C. The conversion ratio to propylmagnesium bromide in the solution was confirmed by analysis using gas chromatography and found to be 5%. The solution was passed through the magnesium packed tower under the same conditions. The conversion ratio to propylmagnesium bromide in the solution having passed the packed tower was confirmed by analysis using gas chromatography and found to be 11%.

Example 10

Four magnesium packed towers described above were connected in series using PFA tubes, and the tubes connecting the packed towers were each immersed in a water bath at 30° C., so that the liquid temperature at the inlet of the second or later tubes was 30° C. The mixed solution of tetrahydrofuran and 1-bromopropane described in Example 9 was supplied at 400 mL/min, and the mixed solution was brought into contact with magnesium in each packed tower. During the solution supply, the sample immediately after passing through each packed tower was taken from the sampling valve provided between the packed towers, and the conversion ratio to propylmagnesium bromide was confirmed by analysis by gas chromatography. The conversion ratio was 7% after passing the first tower, 12% after passing the second tower, 20% after passing the third tower, and 29% after passing the fourth tower.

Example 11

The total amount of the solution obtained in Example 10 was further supplied into the four magnesium packed towers connected in series under the same conditions as Example 10 two times. The conversion ratio was 59% after the first supply and 84% after the second supply.

Example 12

To a well-dried 10 L glass bottle, 7.5 L of tetrahydrofuran (water content: 10 ppm), 150 g of 1-bromopropane, and 157 g of dichlorodimethylsilane were charged and mixed by shaking. The resulting mixed solution was supplied to the four magnesium packed towers connected in series under the same conditions as Example 5 three times. Each time the solution was passed through the four magnesium packed towers, the sample was collected and the conversion ratio of the raw material to chlorodimethylpropylsilane was measured by gas chromatography. The conversion ratio was 25% after the first supply, 57% after the second supply, and 89% after the third supply. The temperatures and the results of conversion ratios of the solution discharged from the magnesium packed towers in Example 12 are shown in Table 1.

Example 13

To a well-dried 10 L glass bottle, 7.5 L of tetrahydrofuran (water content: 10 ppm), 246 g of 1,3-dibromopropane, and 315 g of dichlorodimethylsilane were charged and mixed by shaking. The resulting mixed solution was supplied to the four magnesium packed towers connected in series under the same conditions as Example 5 three times. Each time the solution was passed through the four magnesium packed towers, the sample was collected and subjected to analysis. $^1$H-NMR and $^{29}$Si-NMR analyses of the solution after the reaction confirmed that the product was 1,3-di-(dimethylchlorosilyl)propane. The conversion ratio at each stage was determined by the internal standard method (internal standard substance was toluene) by $^1$H-NMR. As a result, the conversion ratio was 24% after the first supply, 51% after the second supply, and 73% after the third supply.

Comparative Example 1

The same procedures as Example 4 were carried out except that 6.0 g of powdery magnesium having an average specific surface area of $3 \times 10^{-3}$ m$^2$/g was used as magnesium to be packed in the packed tower. During the solution supply, the temperature of the solution at the outlet of the packed tower was measured to be 55° C. to 62° C. Since gas contamination was observed in the tube that supplied liquid, it was found that the reaction solution boiled in the packed tower. The conversion ratio to propylmagnesium bromide of the solution after the reaction was analyzed, and found to be 2%.

Comparative Example 2

The same procedures as Example 7 were carried out except that 6.0 g of powdery magnesium having an average specific surface area of $3 \times 10^{-3}$ m$^2$/g was used as magnesium to be packed in the packed tower. Similarly to Comparative Example 1, since gas contamination was observed in the tube that supplied liquid, it was found that the reaction solution boiled in the packed tower. As with Example 7, analysis was performed to determine the conversion ratio to chlorodimethylpropylsilane, and it was found that the conversion ratio was 18% after the first supply, 24% after the second supply, and 28% after the third supply. The temperatures and the results of conversion ratios of the solution discharged from the magnesium packed towers in Comparative Example 2 are shown in Table 1.

TABLE 1

| | | | Example 7 | Example 12 | Comparative Example 2 |
|---|---|---|---|---|---|
| Specific surface area of magnesium (m$^2$/g) | | | $5.8 \times 10^{-5}$ | $9.0 \times 10^{-5}$ | $3.0 \times 10^{-3}$ |
| First supply | Solution temperature at the outlet of each packed tower (° C.) | First packed tower | 42~44 | 44~46 | 59~61 |
| | | Second packed tower | 42~46 | 45~49 | 58~62 |
| | | Third packed tower | 43~45 | 50~52 | 59~63 |
| | | Fourth packed tower | 44~48 | 51~54 | 31~43 |
| | Conversion ratio(%) | | 28 | 25 | 18 |
| Second supply | Solution temperature at the outlet of each packed tower (° C.) | First packed tower | 38~44 | 42~46 | 32~34 |
| | | Second packed tower | 39~43 | 43~44 | 33~35 |
| | | Third packed tower | 40~42 | 42~45 | 32~36 |
| | | Fourth packed tower | 37~43 | 40~44 | 32~34 |
| | Conversion ratio (%) | | 54 | 57 | 24 |
| Third supply | Solution temperature at the outlet of each packed tower (° C.) | First packed tower | 35~39 | 38~42 | 32~34 |
| | | Second packed tower | 34~35 | 39~41 | 33~34 |
| | | Third packed tower | 36~37 | 35~39 | 32~36 |
| | | Fourth packed tower | 32~34 | 31~36 | 32~33 |
| | Conversion ratio(%) | | 84 | 89 | 28 |

The invention claimed is:

1. A method for producing a halogenated hydrocarbon magnesium compound, the method comprising contacting a halogenated hydrocarbon compound with magnesium having a specific surface area of $1 \times 10^{-5}$ to $2 \times 10^{-4}$ m$^2$/g.

2. The method for producing a halogenated hydrocarbon magnesium compound according to claim 1,
wherein the halogenated hydrocarbon compound is at least one selected from a mono-halogenated alkyl compound and a di-halogenated alkyl compound represented by the following formula (1):

X—R—X (1)

wherein R represents a linear or branched alkyl group having 1 to 8 carbon atoms and X represents a halogen atom.

3. The method for producing a halogenated hydrocarbon magnesium compound according to claim 1, wherein the halogenated hydrocarbon compound is a hydrocarbon bromide compound.

4. The method for producing a halogenated hydrocarbon magnesium compound according to claim 1, wherein the halogenated hydrocarbon compound is contacted with the magnesium at a temperature between −78° C. and 100° C.

5. The method for producing a halogenated hydrocarbon magnesium compound according to claim 1, wherein a solution containing the halogenated hydrocarbon compound is contacted with the magnesium.

6. The method for producing a halogenated hydrocarbon magnesium compound according to claim 5, wherein the solution containing the halogenated hydrocarbon compound is passed through a packed tower filled with the magnesium.

7. The method for producing a halogenated hydrocarbon magnesium compound according to claim 6, wherein the solution containing the halogenated hydrocarbon compound is repeatedly passed through the packed tower filled with the magnesium.

8. The method for producing a halogenated hydrocarbon magnesium compound according to claim 6, wherein a plurality of packed towers each filled with the magnesium exist and the solution containing the halogenated hydrocarbon compound is passed through the plurality of packed towers.

9. The method for producing a halogenated hydrocarbon magnesium compound according to claim 6, wherein the solution containing the halogenated hydrocarbon compound has a temperature between −78° C. and 100° C.

10. A method for producing a tertiary alcohol compound, comprising:
    producing a halogenated hydrocarbon magnesium compound by the method according to claim 1, and
    contacting the halogenated hydrocarbon magnesium compound with a ketone compound.

11. A method for producing an organosilicon compound, comprising:
    producing a halogenated hydrocarbon magnesium compound by the production method according to claim 1, and
    contacting the halogenated hydrocarbon magnesium compound with a silicon compound selected from a chlorosilane compound and an alkoxysilane compound.

* * * * *